(12) United States Patent
Martins et al.

(10) Patent No.: US 9,247,927 B2
(45) Date of Patent: Feb. 2, 2016

(54) DOPPLER ULTRASOUND IMAGING

(71) Applicant: B-K MEDICAL APS, Herlev (DK)

(72) Inventors: Bo Martins, Rødovre (DK); John Antol, Nahant, MA (US); Claus Brøchner Nielsen, Kbh. S. (DK)

(73) Assignee: B-K Medical Aps, Herlev (DK)

( * ) Notice: Subject to any disclaimer, the term of this patent is extended or adjusted under 35 U.S.C. 154(b) by 214 days.

(21) Appl. No.: 13/838,329

(22) Filed: Mar. 15, 2013

(65) Prior Publication Data

US 2014/0276072 A1    Sep. 18, 2014

(51) Int. Cl.
*A61B 8/00* (2006.01)
*A61B 8/08* (2006.01)
*A61B 8/06* (2006.01)

(52) U.S. Cl.
CPC . *A61B 8/488* (2013.01); *A61B 8/06* (2013.01); *A61B 8/0891* (2013.01); *A61B 8/463* (2013.01); *A61B 8/5223* (2013.01); *A61B 8/54* (2013.01)

(58) Field of Classification Search
CPC ........ A61B 8/488; A61B 8/06; A61B 8/0891; A61B 8/463; A61B 8/5223; A61B 8/54
USPC .................................... 600/437–469
See application file for complete search history.

(56) References Cited

U.S. PATENT DOCUMENTS

| | | | |
|---|---|---|---|
| 5,544,658 A * | 8/1996 | Kim et al. | 600/455 |
| 6,679,847 B1 * | 1/2004 | Robinson et al. | 600/447 |
| 6,682,483 B1 * | 1/2004 | Abend et al. | 600/437 |
| 2004/0019278 A1 * | 1/2004 | Abend | 600/454 |
| 2004/0267127 A1 * | 12/2004 | Abend et al. | 600/450 |
| 2005/0004461 A1 * | 1/2005 | Abend | 600/437 |
| 2008/0119735 A1 * | 5/2008 | Lin et al. | 600/450 |
| 2008/0306386 A1 * | 12/2008 | Baba et al. | 600/455 |
| 2009/0030321 A1 * | 1/2009 | Baba et al. | 600/454 |
| 2011/0196237 A1 * | 8/2011 | Pelissier et al. | 600/454 |

* cited by examiner

*Primary Examiner* — Sanjay Cattungal
(74) *Attorney, Agent, or Firm* — Anthony M. Del Zoppo, III; Driggs, Hogg, Daugherty & Del Zoppo, Co., LPA

(57) ABSTRACT

An ultrasound imaging system includes a vector flow imaging processor that processes ultrasound data representing structure flowing through a tubular object and generates vector flow imaging information for a region of interest of the tubular object that is indicative of the structure flowing through a tubular object based thereon and processing circuitry that determines at least one parameter for Doppler imaging based on the vector flow imaging information.

29 Claims, 5 Drawing Sheets

DOPPLER ULTRASOUND IMAGING

TECHNICAL FIELD

The following generally relates to ultrasound and more particularly to Doppler ultrasound imaging.

BACKGROUND

Doppler (D) ultrasound imaging has been used to measure velocity of flow of blood cells inside a defined sub-portion of a blood vessel of interest. The Doppler gate (which defines the Doppler sample volume) has been manually placed using B mode imaging and in connection with color flow mapping (CFM), for example, in a B+CFM duplex mode. The CFM shows relative blood flow direction, determined based on a phase shift between returning frequencies and transmitted frequency, with positive shifts indicating blood is moving away from the transducer, and negative shifts indicating blood is moving towards the transducer.

For this, the transducer is positioned so that the B mode image shows the blood vessel of interest, and the CFM is superimposed there over. The user then places the gate along a line of insonation about a cross section of the vessel, using the CFM as a guide.

Velocity is calculated from the Doppler frequency shift according to EQUATION 1:

$$V = \frac{C}{2f_o \cos\psi} \Delta f. \quad \text{EQUATION 1}$$

where V represents flow velocity, $\Delta f$ represents the Doppler shift, $f_o$ represents the original transmit frequency, C represents the speed of sound in soft tissue, and $\psi$ represents the angle between the beam and the blood flow. From EQUATION 1, V is inversely proportional to $\cos \psi$, and the calculation of V approaches zero (0) as $\psi$ approaches ninety degrees (90°) (i.e., cos 90=0). An angle of approximately forty-five degrees (45°) to sixty degrees (60°) has been used to obtain velocity estimations.

In order to reduce measurement inaccuracy, the measurement situation is modified via electronic steering and/or manual maneuvering of the transducer elements so that the Doppler angle is approximately forty-five degrees (45°) to sixty degrees (60°).

Angle correction is the process of determining the correct value of $\psi$. For this, a user-turnable indicator (angle correction) marks the direction of the flow in the color flow mapped image at an approximate center region of the gate. The user eyeballing the vessel in the B-mode image then turns the angle correction indicator until it is aligned with the vessel walls. Having done so, the system calculates the angle between insonation and angle correction indicator. The beam is electronically steered by adjusting the transmit and/or receive profile of the transducer elements or mechanically adjusted until $\psi$ is approximately forty-five degrees (45°) to sixty degrees (60°). The possibilities of electronic steering (Doppler steering angle) are typically limited to three choices, e.g. −20 degrees, 0 degrees, or +20 degrees. Angle correction changes $\psi$ in the EQUATION 1, resulting in a different estimate of the velocity of the blood.

The sensitivity of the Doppler and of the color flow mapping is determined by the pulse repetition frequency (PRF). A sufficiently high PRF is needed to prevent ambiguous velocity estimates (aliasing), but an unnecessarily high PRF will cause the frequency shift for slow flow to be less accurate or even go undetected. Therefore the user will typically adjust the PRF by viewing the color flow map image looking for signs of aliasing.

The output of the Doppler processing is presented not only as maximum or mean velocities but also as a spectrum. The spectrum represents clinical information in a form that a trained user can recognize as an image. Approximately half of the time the spectrum will be presented in a manner that the user can readily understand, the other half of the time the spectrum will be inverted, so that the systolic peaks are pointing downwards. In the latter case, the user will manually invert the spectrum to keep the spectrum above the baseline.

The peak systolic velocity of the internal carotid artery is clinically used as an indicator for the likelihood of a future stroke. To determine the point of highest velocity, the user from the color flow map first tries to identify the approximate point of highest velocity. The highest velocity within a color region of interest is not always evident. Therefore, the user will typically manually move the Doppler gate around in the chosen area to find the highest Doppler shift/velocity.

Volume flow rate has been used for some applications such as dialysis graft assessment. The volume flow rate may be computed using a time average mean velocity of the blood cells passing through the opening of the Doppler gate multiplied with an area of a cross-section of the vessel, as shown in EQUATION 2:

$$Q = v_{TAM} \pi \left(\frac{d}{2}\right)^2, \quad \text{EQUATION 2}$$

where Q is the volume flow rate, $v_{TAM}$ is the time average mean velocity of the blood cells passing through the gate opening having a speed above the cut-off value determined by the setting of the Doppler Wall filter, and d is the vessel diameter. Outside the vessel, the speed of the scatterers is zero, so $v_{TAM}$ is the same as if the Doppler gate had been adjusted to only cover the vessel. To determine the vessel's cross-section area, the diameter d is used. The diameter is manually determined by the user eyeballing the location of the inner wall of the vessel at the Doppler gate. Then the user manually measures the diameter. Accurate determination of the diameter is particularly important because the volume flow rate is proportional to the square of the diameter.

Prior to the Doppler measurement, the Doppler sample volume size (Doppler gate) must have been set to encompass the entire vessel. If the sample volume size is too small, the average velocity estimate may be too large because the gate then only incorporates the flow in the center of the vessel, and if the sample volume size is too large, the Doppler may pick up signal from more than the one vessel being the target for volume flow rate estimation. Likewise, if angle correction is not employed or not accurate, the velocity estimate may be erroneous (too large or too small), as the denominator of EQUATION 1 increases (or decrease) with decreasing (or increasing) angle. Moreover, manually identification of the vessel diameter is subject to operator error, and may lead to an erroneous volume flow rate.

SUMMARY

Aspects of the application address the above matters, and others.

In one aspect, an ultrasound imaging system includes a vector flow imaging processor that processes ultrasound data representing structure flowing through a tubular object and generates vector flow imaging (VFI) information for a region of interest of the tubular object that is indicative of the structure flowing through a tubular object based thereon and processing circuitry that determines at least one parameter for Doppler imaging based on the vector flow imaging information.

In another aspect, a method includes obtaining vector flow imaging information for a region of interest of a tubular object that is indicative of structure flowing through the tubular object based on ultrasound data representing the structure flowing through the tubular object and determining a Doppler gate location in the region of interest based on the vector flow imaging information.

In another aspect, a method includes obtaining vector flow imaging information for a region of interest of a tubular object that is indicative of structure flowing through the tubular object based on ultrasound data representing the structure flowing through the tubular object and determining a volume flow rate parameter value for flowing structure within a Doppler gate based on the vector flow imaging information In another aspect, a method for conducting a vascular Doppler study using single hand operation, includes receiving an input indicative of actuation of a physical control by an object carrying a transducer array for the vascular Doppler study, and activating both Doppler gate placement and image or image sequence and measurement capture in response to receiving the input.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following describes an approach that uses vector flow imaging (VFI) to identify a position of peak blood flow velocity in a sub-portion of a blood vessel of interest and automatically place a Doppler gate about that point, determine a Doppler steering angle, determine a direction of the flow at this position and automatically adjust a Doppler angle correction accordingly, potentially adaptively adjust the Doppler sample volume size (Doppler gate) to the size of the vessel, invert the Doppler spectrum if needed and potentially automatically determine and display in real time an indicator for the diameter of the vessel within the Doppler gate and estimate a volume flow rate based thereon.

Figure 1:
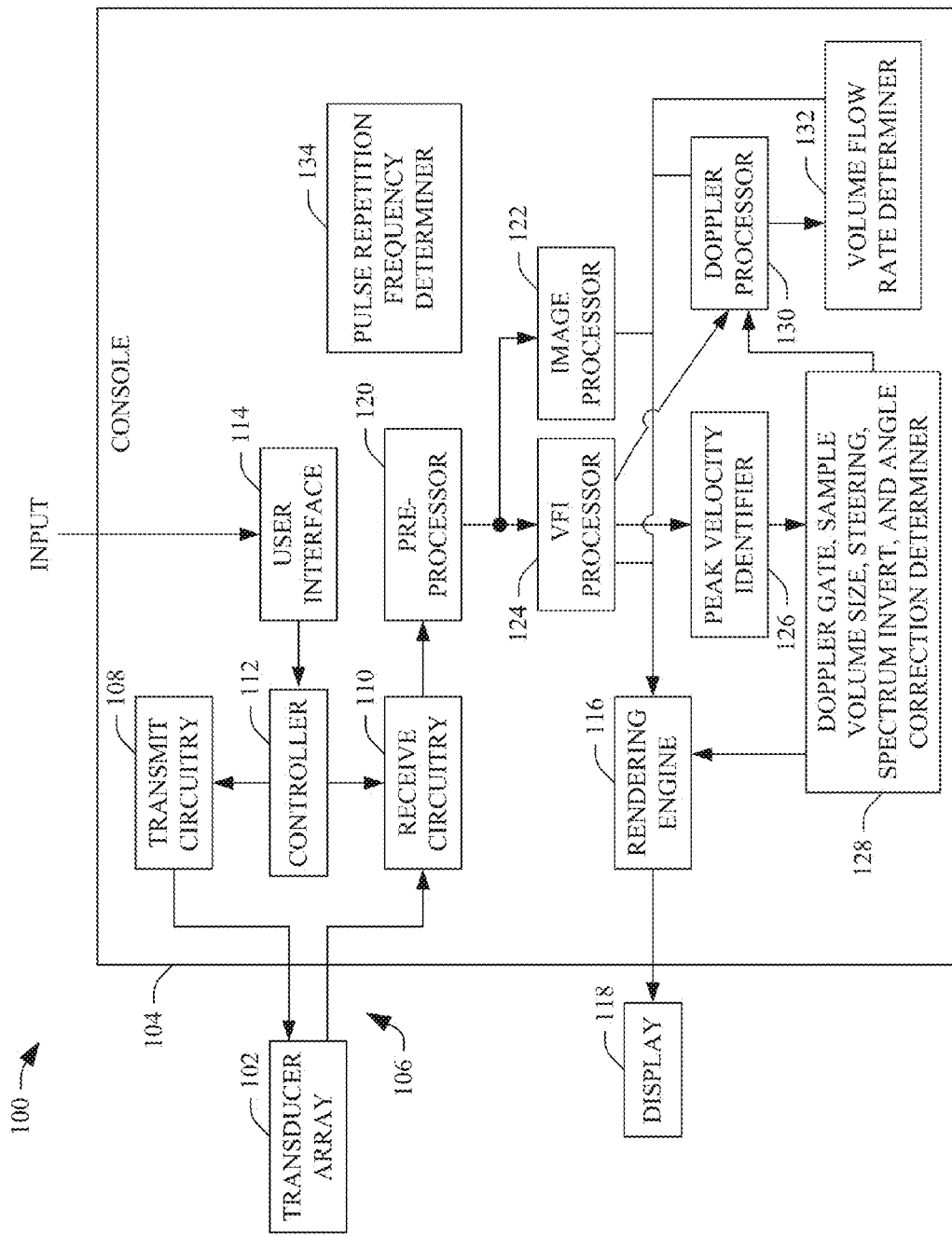
FIG. 1 schematically illustrates an example ultrasound imaging system configured to operate in at least B mode, VFI mode, and D mode.

FIG. 1 schematically illustrates an example ultrasound imaging system 100. The system 100 includes a transducer array 102 and a console 104. The transducer array 102 and the console 104 communicate with each over a communications channel 106, which may include a hardwired and/or wireless communications channel. It is to be appreciated that the ultrasound imaging system 100 may be a hand held, a portable (e.g., on a cart with wheels), and/or a stationary system, and/or the console 104 can be a separate computer.

The transducer array 102 converts an electrical signal to an ultrasound pressure field and vice versa. More specifically, the transducer array 102 includes an array of multiple transducer elements that are configured to transmit ultrasound signals and receive echo signals. Examples of suitable arrays include 32, 128, 192, and/or other elements arrays, including square and rectangular arrays. The array can be linear, curved, and/or otherwise shaped, fully populated, sparse and/or a combination thereof, etc.

Transmit circuitry 108 generates a set of pulses (or a pulsed signal) that are conveyed to the transducer array 102. The set of pulses excites a set of the transducer elements of the transducer array 102, causing the excited transducer elements to transmit ultrasound signals into an examination or scan field of view. In one instance, the transmit ultrasound signals traverse structure flowing through a portion of a blood vessel of interest in the scan field of view and blood cells flowing therein.

Receive circuitry 110 receives a set of echoes (or echo signals) generated in response to the transmitted ultrasound signals, for example, in response to the ultrasounds field traversing structure such as blood cells flowing in a portion of a vessel and/or organ cells in a region of interest in the scan field of view and/or other structure.

A controller 112 controls the transmit circuitry 108 and the receive circuitry 110. Such control can be based on a mode of operation. Examples of modes of operation include, but are not limited to, B-mode, B+VFI duplex mode, B+VFI+D triplex mode, and/or other modes.

A user interface (UI) 114 includes one or more input devices (e.g., a button, a knob, a slider, a touch pad, a mouse, a trackball, a touch screen, etc.) and/or one or more output devices (e.g., a display screen, a light, an audio generator, etc.), which allow for interaction between a user and the ultrasound imaging system 100. By way of non-limiting example, the user interface (UI) 114 may include a feature to activate B-mode, VFI mode, D mode, automatic gate positioning, automatic angle correction, and/or other feature of the system 100, individually or in combination.

A rendering engine 116 visually presents processed data via a display 118. As described in greater detail below, this may include visually displaying one or more of B-mode, VFI mode, D mode, and/or other mode information, individually or in combination. For example, in one instance, a B-mode image is displayed with VFI information superimposed there over, concurrently with indicia showing a Doppler gate, a direction of flow at the Doppler gate, a correction angle, points on an inner wall of the vessel defining the vessel diameter, etc.

A pre-a processor 120 processes received sets of echoes. Suitable processing includes applying time delays to echoes, weighting echoes and summing delayed and weighted echoes, applying echo-cancellation, wall-filtering, base banding, averaging and decimating, producing beams to estimate an axial velocity component and a lateral velocity component, lower speckle and/or improve specular reflector delineation, perform FIR and/or IIR filtering, and/or pre-processing.

An image processor 122 processes the pre-processed data and generates one or more images. In the illustrated embodiment, the image processor 122 at least generates B mode images. The generated one or more images, as shown, can be conveyed to the rendering engine 116 and displayed via the display 118.

A VFI processor 124 processes the pre-processed data and generates vector flow imaging (VFI) information for the entire B mode image or a predetermined sub-region of the image that includes a sub-portion of the vessel of interest. This includes determining axial and lateral velocity components of the flowing blood cells, which indicates both direction and magnitude. An example of an approach for determining these components is described in U.S. Pat. No. 6,859,659 B1 to Jensen, filed on Nov. 9, 2001, and entitled "Estimation of Vector Velocity," which is incorporated herein by reference in its entirety.

Other approaches for determining the axial and lateral velocity and/or other components are also contemplated herein. Generally, any approach for determining the VFI information can be used herein. The VFI information, as shown, can be conveyed to the rendering engine 116 and displayed via the display 118. In one instance, the VFI information is superimposed over the displayed B mode image. The displayed VFI information can be updated as new VFI information is generated. The VFI information can be displayed using indicia such as arrows (with heads indicating direction and tail lengths indicating magnitude), color, gray scale, and/or other indicia.

A peak velocity identifier 126 evaluates the VFI information and identifies a peak velocity (e.g., a peak systolic or other velocity) and a location thereof. In one non-limiting instance, the peak velocity identifier 126 identifies the location of a peak velocity as follows. The magnitude for each VFI sample is stored in a cyclic array, which covers a predetermined number of frames (e.g., 64, 128, 512, etc.). For each frame, the magnitude measurements corresponding to each position (line, sample) are added. The sample location corresponding to the largest sum is selected as the location of the maximum flow.

If there is no specific hotspot in the flow, the algorithm may select the same or a different location each time. In this case, the location will likely be stable after 4-6 and/or other number cardiac cycles. If the input is aliased, the best spot can still be identified, for example, by omitting frames likely aliasing from the average calculation. For example, frames for which one or more samples have a value that is close to the aliasing limits for the VFI data (the aliasing limit may be different for the horizontal and vertical VFI components). If excluding these frames results in less than a predetermined number of frames, then no frames are omitted.

A Doppler gate, sample volume size, steering, spectrum invert, and angle correction (Doppler parameter) determiner 128 places the Doppler gate about the peak velocity identified by the peak velocity identifier 126. When in B+VFI mode, actuating Doppler via the user interface 114 invokes the Doppler gate, sample volume size, steering, spectrum invert, and angle correction determiner 128 to place the Doppler gate. When in B+VFI+D mode, actuating gate placement via the user interface 114 invokes the Doppler gate, sample volume size, steering, spectrum invert, and angle correction determiner 128 to place the Doppler gate.

Placing the Doppler gate includes, in one instance, placing it so that it covers an entirety of the cross section of the vessel. In another embodiment, Doppler gate is placed so that it covers at least a portion of the cross section of the vessel. The Doppler gate, sample volume size, steering, spectrum invert, and angle correction determiner 128 generates a signal indicative of the Doppler gate and conveys this signal to the rendering engine 116, which displays the Doppler gate in connection with the B mode image and VFI information.

Briefly turning to FIGS. 2, 3, 4 and 5, several examples of the placement of the Doppler gate are illustrated.

Figure 2:
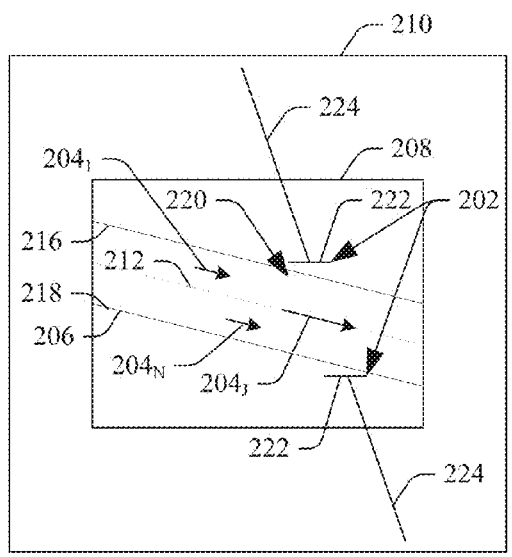
FIG. 2 illustrates an example Doppler gate symmetrically disposed about a peak velocity located at a center of a vessel and covering the entire cross section of the vessel.

In FIG. 2, a Doppler gate 202 is symmetrically disposed about an identified peak flow $204_J$ (of a pluralities of flows $204_1, \ldots, 204_N$, where J and N are integers) of a portion of a vessel 206 in a predefined region 208 within a B mode image 210. The identified peak flow 204 is at a center line 212 of the vessel 206 and, thus, the Doppler gate 202 is located at approximately the center region 212. In this example, the Doppler gate 202 extends from approximately just outside a first wall 216 to a second wall 218 of the vessel 206, covering the entire cross section of the vessel 206. A region 220 between poles 222 of the Doppler gate 202 defines the sample region. Line 224 represents a line of insonation.

Figure 3:
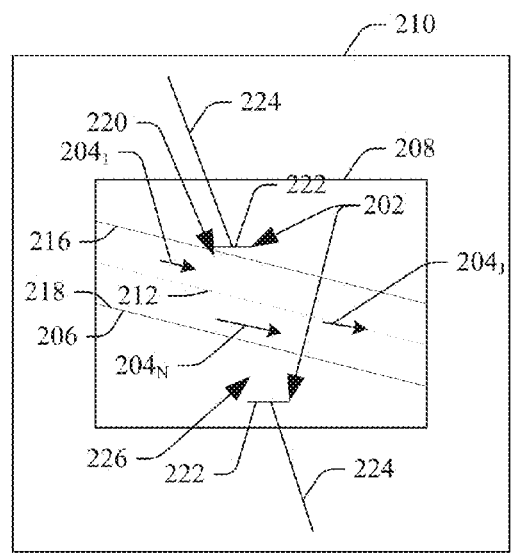
FIG. 3 illustrates an example Doppler gate symmetrically disposed about a peak velocity that is not located at a center of the vessel, but still covers the entire cross section of the vessel, as well as a non-vessel region.

In FIG. 3, the Doppler gate 202 is symmetrically disposed about the identified peak flow $204_N$, which is not located at approximately the center line 212 of the vessel 206. In this case, a width of the Doppler gate 202 is increased so that the Doppler gate 202, similar to FIG. 2, covers the entire cross section of the vessel 206. As a consequence, a region 226 outside the vessel 206 is also located within the poles 222 of the Doppler gate 202.

Figure 4:
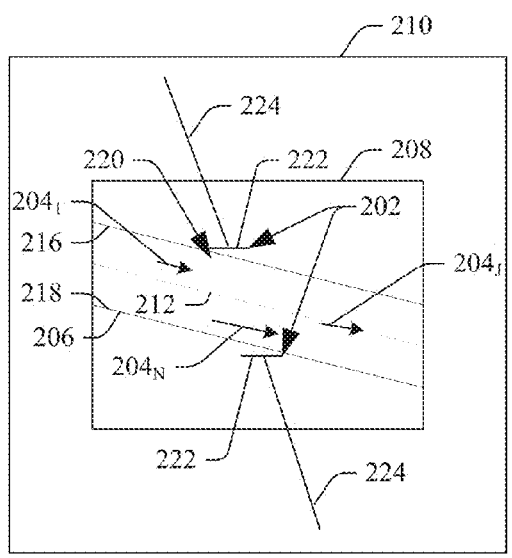
FIG. 4 illustrates an example Doppler gate asymmetrically disposed about a peak velocity that is not located at a center of the vessel and covers the entire cross section of the vessel, minimizing non-vessel region within the gate.

In FIG. 4, the Doppler gate 202 is asymmetrically disposed about the identified peak flow $204_N$ so that it extends from approximately just outside the wall of the vessel 206 and covers the entire cross section of the vessel 206. In this example, a user, via the interface 114, can adjust the position of the sample region 220, with the poles 222 following the vessel boundaries so that they are always just outside the wall. This embodiment mitigates picking up unwanted signal from the region 226 (FIG. 3) between the vessel 206 and the poles 222.

Figure 5:
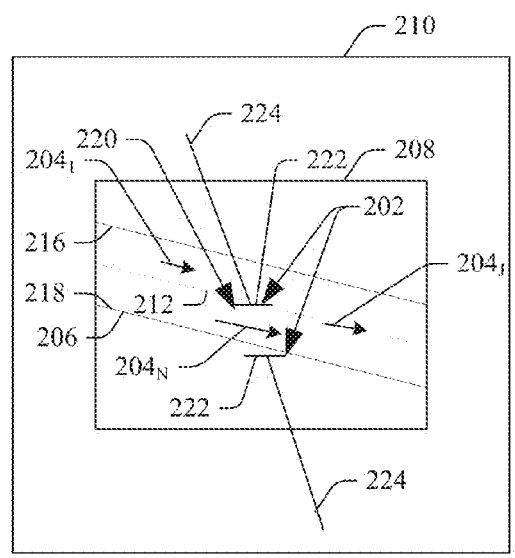
FIG. 5 illustrates an example Doppler gate symmetrically disposed about a peak velocity that is not located at a center of the vessel, where the gate does not cover the entire cross section of the vessel.

In FIG. 5, the Doppler gate 202 is symmetrically disposed about the identified peak flow $204_N$ to minimize the region 226 (FIG. 3). However, as a consequence, the Doppler gate 202 does not cover the entire cross section of the vessel 206. This configuration is not well suited for providing data for volume flow rate measurements. With FIGS. 2-5, the user, via the user interface 114, can accept, request re-determination of, and/or manually place the Doppler gate 202.

Returning to FIG. 1, when Doppler gate placement is first activated, for example, based on an input to the user interface 114 as well as later on based on the VFI real-time information, the Doppler gate, sample volume size, steering, spectrum invert, and angle correction determiner 128 also sets the proper Doppler steering angle to minimize the angle $\psi$ between the Doppler ultrasound beam direction and the estimated direction of the flow at the Doppler gate, which may or may not be sufficient to achieve a Doppler angle (angle correction) of about forty-five (45°) to sixty degrees (60°).

Figure 6:
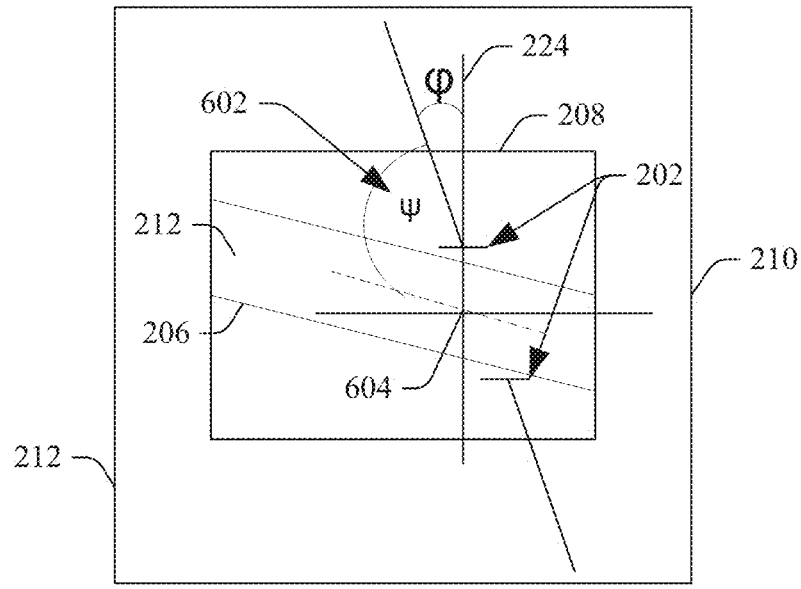
FIG. 6 illustrates angle correction.

An example of the angle correction is illustrated in connection with FIG. 6. In FIG. 6, the slope of the flow 604 is down to right. This can be detected by the sign of the axial and vertical velocity components at the Doppler gate. Consequently, the steering angle φ is selected so that the line of insonation 224 points down to the right, thereby minimizing the angle 602 used to angle correct the Doppler measurement. In another instance than depicted in FIG. 6, the choices of possible steering angles might be limited if the Doppler gate were positioned very close to the edge of the color box. In any case, the proper Doppler steering is automatically selected and activated simultaneously with the placement of the gate itself by the Doppler gate, sample volume size, steering, spectrum invert, and angle correction determiner 128. In one instance, Doppler steering covers an angular range of ±20°. Additional angular adjustment can be through manual heal and toeing of the transducer array.

The Doppler gate, sample volume size, steering, spectrum invert, and angle correction determiner 128 generates a signal indicative of the direction of flow 604 and the angle correction to the rendering engine 116, which displays this information in connection with the B mode image, the VFI information and the Doppler gate. This information can be continuously generated, updated and displayed so that user knows whether the Doppler measurement will achieve the Doppler angle between forty-five (45)° and sixty degrees (60°).

Generally, the angle of the flow with horizontal is estimated from the ratio between the vertical and horizontal components of the VFI data at the gate location over a short window of time. The angle can be manually adjusted on a frozen image. The following describes a more detailed approach for determining the angle correction automatically.

The VFI data is quantized to 4, 8, 32, etc. bits, including sign. Multiple measurements may be taken to determine axial and/or lateral components. The angle of a particular vector may fluctuate over the cardiac cycle if the horizontal component is less sensitive than the vertical component. If that is the case, the lateral velocity component will also be is more dependent on the selected pulse-repetition frequency (PRF) than the axial component. In diastole, the velocity is lower than at the systole, which is what the PRF is targeted for. So in the diastole, the lateral component would then have a tendency to die out causing the estimated angle to appear numerically too large.

With an average algorithm, the vertical components are added over a number of cardiac cycles and the horizontal components are added over the same amount of frames to estimate the angle. A circular buffer includes the statistics of all the possible vector positions for a latest set of a predetermined number of frames. In this example, two positions are investigated, the current position of the Doppler gate and the position that is believed to be the best position. For each of these positions, we sum over the number of frames, L=K*M, corresponding to K cardiac cycles, where K is typically 4, as shown in EQUATION 3:

$$\theta = a\tan(\text{sum}\_1\char`\^L(\Delta y)/\text{sum}\_1\char`\^{\Delta L}(\Delta x)). \quad \text{EQUATION 3:}$$

The approximate frequency of the cardiac cycle may be estimated by computing a (partial) Discrete Fourier Transform of the squared magnitude for the data in the angle estimation buffer.

One preset gives approximately 20 fps. The pulse is somewhere between 40-120, typically 60. If the pulse is 60, there are approximately M=20 frames between the systolic peaks. The frequency component of highest peak in the amplitude of the spectrum estimates this number: M=N/arg{Max(|X(k)|^2)}, where k is the integer frequency index and X is the DFT of the time series of the N=VfiTimeWindow latest recording of max((Δx)^2+(Δy)^2). M can be determined by finding a maximum of the N sample values and then looking for other maxima approximately z*M away from this number, where z is an integer.

With a systolic maxima algorithm, a partial Fourier analysis is applied to the velocity data for the current Doppler gate position to determine the heart frequency and approximate location of the systolic maxima and refine the search for the actual systolic peaks by searching around locations of the expected maxima. The angle of the flow is estimated as shown in EQUATION 4:

$$\theta = a\tan(\text{sum}\_1\char`\^J(\Delta y)/\text{sum}\_1\char`\^J(\Delta x)), \quad \text{EQUATION 4:}$$

where J denotes the number of systolic maxima. In one non-limiting instance, this number is 8 or 13 for a buffer of a predetermined size. The variation, in one instance, is based on the number of frames between the systolic maxima, which may be related to different numbers of C-lines in the images.

With a combined maxima algorithm, for sloped vessels, where the potentially uneven balance between the sensitivity of the horizontal and vertical component becomes more pronounced, a reliable method is to use only the velocity estimates at the systolic peaks (where the velocity is the largest) because the PRF is selected for precisely for the peak systolic velocity.

The average algorithm works well at horizontal orientation also with uneven sensitivity between the vertical and horizontal velocity components, because the vertical component being so small would have a tendency to die out leaving the system better balanced throughout the cardiac cycle. Rather than trying to identify the cases for which one or the other algorithms work best on the average it is possible to use the result of the algorithm that produces the smallest absolute value of the angle.

The need for inversion of the Doppler spectrum can be uniquely determined from the sign of θ and the sign of the horizontal velocity component at the position of the Doppler gate. The Doppler gate, sample volume size, steering, spectrum invert, and angle correction determiner 128 uses this information to invert the spectrum in real time.

In one instance, the Doppler gate, sample volume size, steering, spectrum invert, and angle correction determiner 128 processes the VFI information prior to activating Doppler. For example, once the user is satisfied with the predicted angle correction, Doppler mode can be activated, for example, based on an input to the user interface 114 activating Doppler mode.

The Doppler processor 130 can generate information about the power spectral density of the received blood flow Doppler-shift frequencies, for example, in the form of a 2D spectrogram, which provides the Doppler frequency-shift as a function of time. The Doppler processor 130 generates a signal indicative of the spectrogram to the rendering engine 116, which displays this information in connection with the B mode image, the VFI information, the Doppler gate, and the flow direction. From the spectrum, a calibrated average velocity of the flow over a cardiac cycle can be obtained for the particular position of the Doppler gate.

A volume flow rate determiner 132 determines a flow rate based the VFI information within the Doppler gate. The volume flow rate specifies the amount of blood cells pass through predetermined region of a blood vessel per time unit (e.g., in units of ml/min). As the flow rate varies with the heart cycle, it is typically indicated by a larger time interval, such as minutes rather than seconds, that the result should be the result as if averaged over an integer number of heart cycles.

For determining flow rate, the volume flow rate determiner 132 first determines a location of the inner walls of the vessel based on the output of the VFI processor 124. Volume flow rate is then computed using an angle-corrected time average mean velocity of the blood cells passing through the opening of the Doppler gate multiplied with the area of a cross-section of the vessel, which is determined based on a diameter determined from the location of the inner vessel wall.

The frames utilized to determine the vessel wall correspond to the times of systolic peak flow as the outline of the vessel is well-defined at these instances of time. The frames corresponding to the maxima are estimated as described herein. For venous flow, the selection of the frames may be less important as the outline is well-defined for most if not all frames. Initially, the top and the bottom of the vessel are estimated independently for each color line.

An example non-limiting algorithm follows:
Step 1:
For each image im1 . . . imN corresponding to N systolic peaks
    For(line=1:numLines)
        Find the mid-point=axial index corresponding to largest velocity Search upwards until velocity is zero. The last axial index of non-zero velocity is defined to be on the top boundary of the vessel.
        From the mid-point, search down-wards until sample of zero lateral velocity is encountered. The last axial index of non-zero lateral velocity is defined to be on the bottom boundary of the vessel.
(A reason for specifying the lower boundary of the vessel as the point for which the lateral velocity component is zero is that mirroring artifacts can occur distal to a lower vessel wall. This is particularly pronounced with the carotid artery.)
Step 2:
Median filter the values estimated for the images im1 to imN corresponding to the N identified systolic peaks:
For(line=1:numLines)
    vesTop(line)=median(vesTop(line,im1), . . . , vesTop(line, imgN)
    vesBot(line)=median(vesBot(line,im1), . . . , vesBot(line, imgN)
Step 3:
Attempt to create a connected vessel wall by median filtering across several (9) image lines:
For(line=1:numLines)
    vesTop(line)=median(vesTop(line-4), . . . , vesTop(line+4))
    vesBot(line)=median(vesBot(line-4), . . . , vesBot(line+4))

Figure 7:
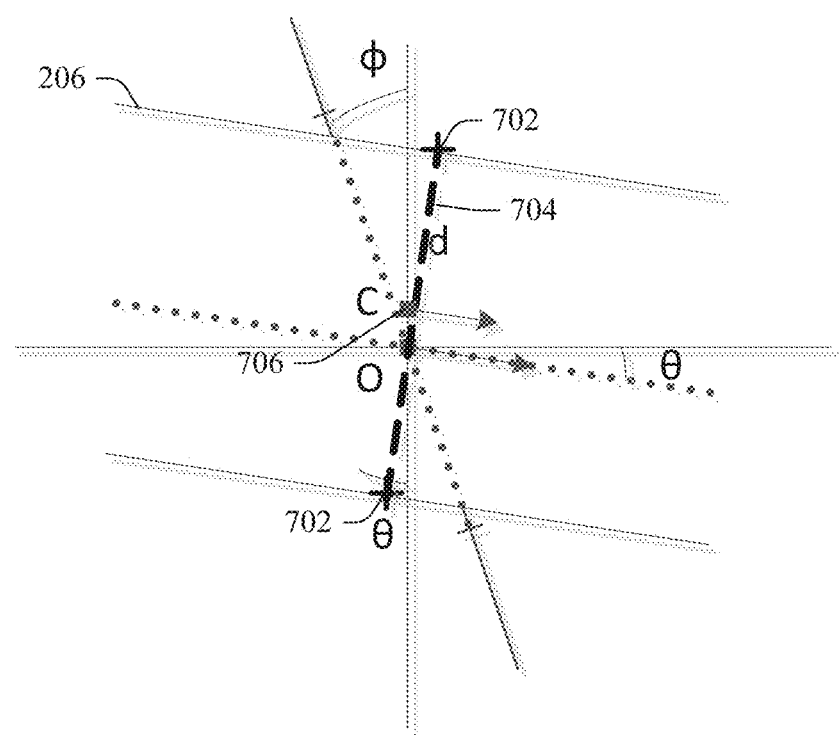
FIG. 7 illustrates vessel diameter determination.

A diameter d is determined from VFI as depicted in Error! Reference source not found. The angle $\theta$ is the angle estimated from VFI data between a horizontal and the direction of the flow. In FIG. 7, two points 702 on the estimated inner vessel walls are marked for visual verification of the correct calculation of the vessel diameter d. The positions of the markers 702 is found by traversing the samples on the estimated upper and lower vessel boundaries picking the points so that a line 704 through the gate center (C) 706 and the point would most closely have the angle $\theta'$ with the vertical direction.

Having found the samples indicated by the two markers 702, the diameter d is simply calculated to be the distance between them. In FIG. 7, a line 704 connects the two markers 702. The angle $\theta'$ is either equal to the angle $\theta$ or equal to the angle of the flow in the middle of the vessel at the same lateral position of the Doppler gate 202. Which one is chosen depends on the estimated average velocity in the two positions. The position at which the flow angle is estimated is the position of highest average velocity.

The volume flow rate determiner 132 utilizes EQUATION 2 and/or other approach to determine the volume flow rate. The average velocity can be determined from pulsed wave Doppler (PWD). The value estimated from PWD is the axial component which is divided by cos $$\cos\left[\left(\frac{\pi}{2} + \theta + \phi\right)\right]$$

in order to get the magnitude of the velocity. In FIG. 7, $\phi$ (negative by convention in the figure) denotes the steering angle of the Doppler gate and $\theta$ (negative by convention in the figure) denotes the slope of the flow at the sample position of the Doppler gate. The slope of the flow can be considered as identical to the slope of the vessel.

The value of $\theta$ is estimated from the flow as described herein and indicate the value visually by the slope of the angle correction line. The user can adjust the value via the user interface 114. The Doppler processor 126 generates a signal indicative of the inner vessel wall of the vessel, which displays this information in connection with the B mode image, the VFI information, the Doppler gate, and the flow direction. For this, the markers 702 can be visually displayed for visual inspection, acceptance, and/or modification by a user.

Returning to FIG. 1, a pulse repetition frequency determiner 134 determines a pulse repetition frequency (PRF). Generally, if the PRF is too low causing gross aliasing, calculations will produce incorrect results, and if the PRF is too high, the sensitivity is unnecessarily low. The pulse repetition frequency determiner 134 determines a suitable PRF based on the VFI information. The user, via the user interface 114, may enable or disable this functionality. When automatic PRF adjustment is activated, for example, by activating Doppler mode or invoking an update via the user interface 114 will cause the PRF to change if it is calculated to be inappropriate.

The following describes an approach for updating the PRF. This approach is based on detection of the velocity sample of largest magnitude in a frame. In a particular case where the horizontal and vertical values alias at different values, the following can be used: x4yAbs=max(max(abs(x),4*abs(y)), sqrt(x*x+y*y)), where x is the horizontal (transverse) velocity component and y the vertical component. The repetition frequency determiner 134 determines a minimum PRF and selects the smallest available PRF being larger than or equal to the minimum PRF.

If x4yAbs values of 127 or 128 are detected for any frame within the latest 5 cardiac cycles, aliasing may have occurred and therefore the PRF is increased. An increment of 1%-20% such as 5%, 9%, etc. of the minimum PRF can be used. If during a last set of frames, at least the number of frames/4 had recorded values of at least 124, aliasing have likely occurred, and the PRF is increased. An increment of the minimum PRF by 10-50% such as 25%, 30%, etc. can be used.

If there is no reason to suspect aliasing, the PRF may be too high or just right. In that case, the minimum PRF is computed from the current PRF and the highest value of x4yAbs within the last three cardiac cycles (this value is called nAbsMax) as follows:

```
delta = (nAbsMax−124) / 128.0f;
minPrf = ( delta + 1.0f) * current PRF
if ( minPrf >= 0.9f*current PRF) {
    keep current PRF
}
```

This means that the current PRF is used if 112<=nAbsMax<=124 and typically also when 125<=nAbsMax<=126.

Figure 8:
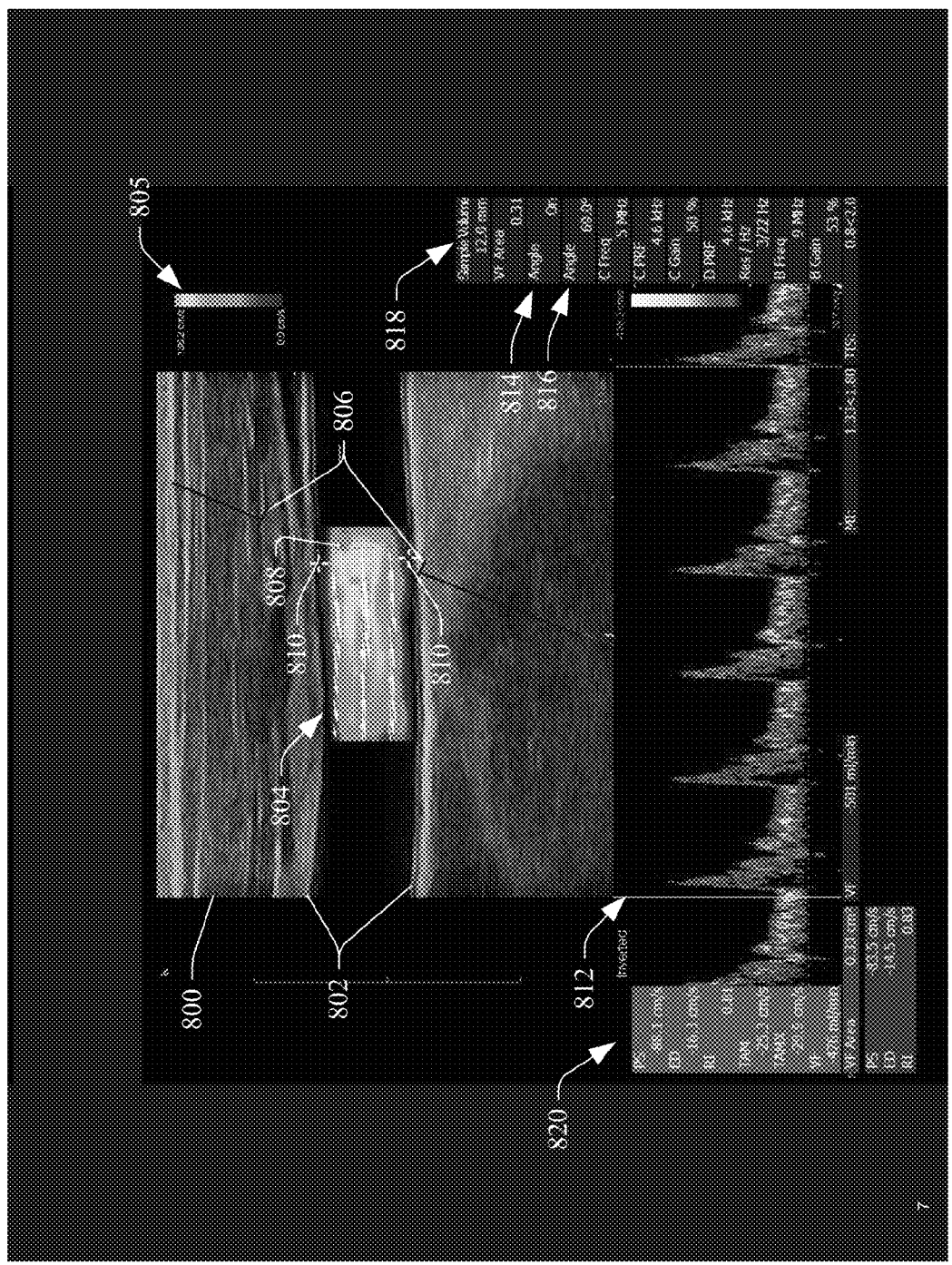
FIG. 8 illustrates a graphical user interface visually presenting B mode, VFI mode and D mode information.

FIG. 8 shows an example graphical user interface (GUI) visually presenting a B-mode image 800 including a portion of a vessel 802, VFI data 804 superimposed there over along with a legend or bar 805 defining a range of velocity values for the VFI data, a Doppler gate 806, a center point 808 of the Doppler gate 806, vessel wall markers 810, a spectrogram 812 (inverted where needed), in indication 814 of whether angle correction is turned on, a value of the angle correction 816 (when angle correction is turned on), and various other information 818 and 820, including the sample volume of the Doppler gate 800, the flow volume area, velocity flow, etc.

It is to be appreciated that one or more of the components of the console 104 can implement via one or more computer processors executing one or more computer readable instructions stored on computer readable storage medium such as physical memory or other non-transitory medium. Additionally or alternatively, at least one of the instructions can be carried by a carrier wave, a signal and/or other transitory medium.

Figure 9:
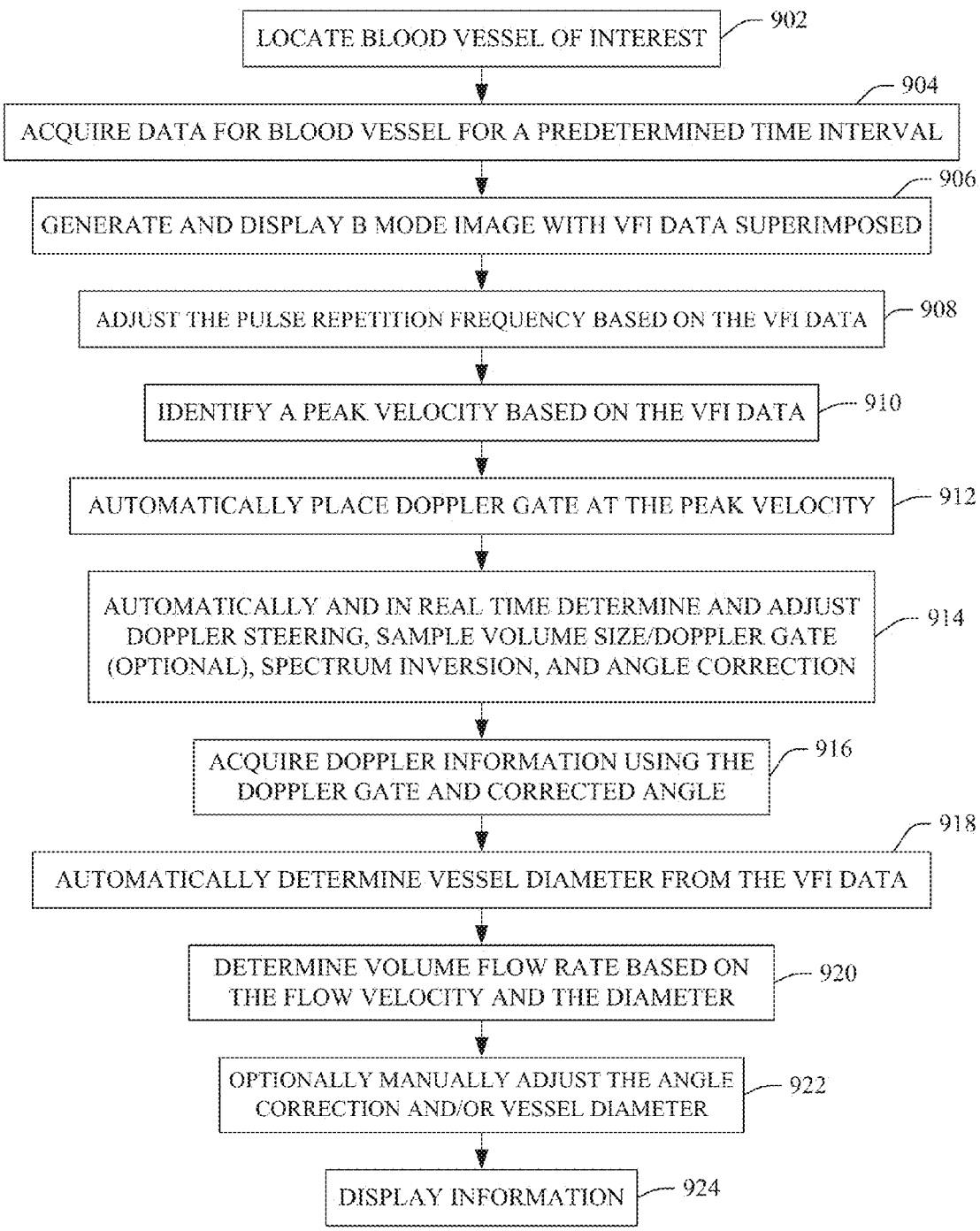
FIG. 9 illustrates an example method for automatically setting the Doppler gate and angle correction based on VFI data and automatically determining the vessel diameter at the Doppler gate.

FIG. 9 illustrates an example method.

It is to be understood that the following acts are provided for explanatory purposes and are not limiting. As such, one or more of the acts may be omitted, one or more acts may be added, one or more acts may occur in a different order (including simultaneously with another act), etc.

At 902, a blood vessel of interest is located via ultrasound scanning.

At 904, data is acquired for the blood vessel of interest over a predetermined time interval.

At 906, a B mode image and VFI data are generated and displayed.

At 908, the pulse repetition frequency is adjusted based on the VFI data.

At 910, a peak flow velocity is identified via the VFI data.

At 912, a Doppler gate is automatically placed at the identified peak flow velocity.

At 914, Doppler steering, optionally sample volume size/Doppler gate, spectrum inversion, and angle correction are automatically determined and adjusted.

At 916, Doppler information is acquired for the Doppler gate.

At 918, a diameter of the vessel is automatically determined based on the VFI data.

At 920, a volume flow rate is determined based on the flow velocity and diameter.

At 922, the angle correction and/or the vessel diameter is optionally manually adjusted.

At 924, the B mode image is displayed along with the VFI data, the Doppler gate, the angle correction, indicia indicating the end points of the vessel diameter, and the volume flow rate.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

Although the above is discussed in connection with blood cells flowing through a blood vessel, it is to be understood that the above also applies to other structure flowing through other tubular objects.

Activation of the gate placement control (possibly repeated) to invoke the desired image and measurements and activation of freeze to capture the image and/or the image sequence and measurements can be through, in one instance, a single key press or, in another instance, multiple key presses. In the former case, this may include a key press that invokes the placement of the Doppler gate followed by an automatic delayed freeze operation. The combined operation could also be: place gate, freeze after a predefined number of seconds, store image and measurements, and unfreeze.

In one instance, the single key press can be through a button on the transducer that provides a physical actuator for the transducer hand. Alternatively, physical possibilities as provided by e.g. a medical foot pedal array, one pedal of which activates Doppler gate placement and another pedal of which freezes/unfreezes the image, would make it possible for the user to obtain the desired image, image sequence and measurements using a single hand and a foot. The foregoing is well-suited for applications such as conducting vascular Doppler studies using single hand operation combined with a possibility for activating a single keyboard control, a transducer button, a foot pedal, or other physical means for activating Doppler gate placement and possibly freezing the image.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound system, comprising:
   a vector flow imaging processor that processes ultrasound data representing structure flowing through a tubular object and generates vector flow imaging information for a region of interest of the tubular object that is indicative of the structure flowing through a tubular object based thereon;
   a peak flow identifier that identifies a peak velocity flow within the region of interest based on the vector flow imaging information;
   a Doppler gate, sample volume size, steering, spectrum invert, and angle correction determiner that places a Doppler gate about the identified peak velocity flow on a displayed image representing the tubular object, wherein the image is generated from the ultrasound data; and
   processing circuitry that determines at least one parameter from Doppler imaging data of a region defined by the Doppler gate based on the vector flow imaging information.

2. The system of claim 1, wherein the vector flow imaging information includes an axial velocity component signal and a lateral component signal, and the axial and lateral component signals indicate a direction and a speed of the structure flowing through the tubular object.

3. The system of claim 1, wherein initially there is no Doppler gate on the image and the vector flow imaging processor generates the vector flow imaging information, and, further comprising:
   a user interface that generates a signal indicative of a user input, wherein in response to the signal the peak flow identifier determines the peak velocity flow and the Doppler gate, sample volume size, steering, spectrum invert, angle correction determiner places the Doppler gate about the peak velocity flow on the image and invokes a Doppler scan using the placed Doppler gate.

4. The system of claim 1, wherein the peak velocity flow is located approximately along a central axis of the tubular object and Doppler gate is placed symmetrically about peak velocity flow and the central axis and covers at least an entirety of a cross section of the object at the Doppler gate.

5. The system of claim 1, wherein the peak velocity flow is located shifted from a central axis of the tubular object and Doppler gate is placed symmetrically about peak velocity flow and covers at least an entirety of a cross section of the object at the Doppler gate.

6. The system of claim 1, wherein the peak velocity flow is located shifted from a central axis of the tubular object and Doppler gate is placed asymmetrically about peak velocity flow and covers at least an entirety of a cross section of the object at the Doppler gate.

7. The system of claim 1, wherein the Doppler gate, sample volume size, steering, spectrum invert, and angle correction determiner further determines a flow direction of the peak flow of the object in the region of interest based on the vector flow imaging information and calculates the best steering angle, potentially adjusts the sample volume size, inverts the spectrum if needed and calculates an adjustment to an angle between insonation and the flow direction so that a Doppler angle is between 45 degrees and 60 degrees with respect to the flow direction.

8. The system of claim 7, further comprising:
a volume flow rate determiner that determines a volume flow rate parameter value for flowing structure within the Doppler gate based on the vector flow imaging information.

9. The system of claim 8, wherein the volume flow rate determiner determines the volume flow rate parameter value based on a diameter of the object within the Doppler gate.

10. The system of claim 8, wherein the volume flow rate determiner determines a location of an inner wall of the object within the Doppler gate based on the vector flow imaging information, determines the diameter based on the inner wall location, and computes the volume flow rate parameter value based on a time average mean velocity of the flowing structure blood cells passing through the Doppler gate multiplied with an area of a cross-section of the object within the Doppler gate, which is determined based on the diameter.

11. The system of claim 8, further comprising:
a repetition frequency determiner that determines a repetition frequency determiner based on the vector flow imaging information.

12. The system of claim 8, further comprising:
a Doppler processor that generates a 2D spectrogram based on the vector flow imaging information.

13. The system of claim 10, further comprising:
a rendering engine that concurrently visually displays the image, the vector flow imaging information, the Doppler gate, the flow direction, the angle correction value, the location of the inner walls, and the volume flow rate parameter value.

14. A method, comprising:
processing, with a vector flow imaging processor, ultrasound data representing structure flowing through a tubular object;
generating, with the vector flow imaging processor, vector flow imaging information for a region of interest of the tubular object that is indicative of the structure flowing through the tubular object based on the processing;
identifying, with a peak flow identifier, a peak velocity flow within the region of interest based on the vector flow imaging information;
placing, with a Doppler gate, sample volume size, steering, spectrum invert, and angle correction determiner, a Doppler gate about the identified peak velocity flow on a displayed image representing the tubular object, wherein the image is generated from the ultrasound data; and
determining, with processing circuitry, at least one parameter from Doppler imaging data of a region defined by the Doppler gate based on the vector flow imaging information.

15. The method of claim 14, wherein the vector flow imaging information includes an axial velocity component signal and a lateral component signal, and the axial and lateral component signals indicate a direction and a speed of the structure flowing through the tubular object.

16. The method of claim 14, wherein the peak velocity flow is located approximately along a central axis of the tubular object and Doppler gate is placed symmetrically about peak velocity flow and the central axis and covers at least an entirety of a cross section of the object at the Doppler gate.

17. The method of claim 14, wherein the peak velocity flow is located shifted from a central axis of the tubular object and Doppler gate is placed symmetrically about peak velocity flow and covers at least an entirety of a cross section of the object at the Doppler gate.

18. The method of claim 14, wherein the peak velocity flow is located shifted from a central axis of the tubular object and Doppler gate is placed asymmetrically about peak velocity flow and covers at least an entirety of a cross section of the object at the Doppler gate.

19. The method of claim 14, further comprising:
receiving an input signal accepting the Doppler gate.

20. The method of claim 14, further comprising:
determining a flow direction of the peak flow of the object in the region of interest based on the vector flow imaging information both in the case that the horizontal and vertical velocity component estimates are equally sensitive and in the case that the horizontal velocity component estimate is less sensitive than the vertical component estimate; and
determining an adjustment to a Doppler steering/insonation angle such that the angle between insonation and the flow direction is between 45 degrees and 60 degrees.

21. The method of claim 20, further comprising:
receiving an input signal accepting the adjustment to the angle.

22. The method of claim 14, further comprising:
concurrently visually displaying the ultrasound image, the vector flow imaging information, the Doppler gate, the flow direction, the angle correction value, the location of the inner walls, and the volume flow rate parameter value.

23. A method, comprising:
obtaining vector flow imaging information for a region of interest of a tubular object that is indicative of structure flowing through the tubular object based on ultrasound data representing the structure flowing through the tubular object,
determining a location of an inner wall of the object with the Doppler gate;
determining a diameter of the object based on the inner wall location; and
determining a volume flow rate parameter value for flowing structure within a Doppler gate based on a time average mean velocity of the flowing structure passing through the Doppler gate multiplied with an area of a cross-section of the object within the Doppler gate, which is determined based on the diameter.

24. The method of claim 23, further comprising:
receiving an input signal accepting the diameter.

25. The method of claim 23, further comprising:
determining a Doppler gate location in the region of interest based on the vector flow imaging information.

26. The method of claim 25, wherein determining the Doppler gate location includes determining a magnitude for each vector flow imaging sample for each frame, adding the magnitude corresponding to each position, and selecting a sample location of the maximum flow corresponding to a largest sum.

27. The method of claim 25, further comprising:
determining a Doppler angle correction based on the vector flow imaging information.

28. The method of claim 27, wherein determining Doppler angle correction includes estimating from a ratio between a vertical component and a horizontal component of the vector flow imaging information at the Doppler gate location over a predetermined time interval.

29. The method of claim 27, further comprising:
concurrently visually displays an ultrasound image, the vector flow imaging information, the Doppler gate, and the volume flow rate parameter value.

\* \* \* \* \*